(12) United States Patent
Yeung (10) Patent No.: US 11,154,652 B2
(45) Date of Patent: Oct. 26, 2021

(54) FLUID MANAGEMENT SYSTEM

(71) Applicant: 8i Research Development Pty Ltd, Castlecrag (AU)

(72) Inventor: Simon Yeung, Brookvale (AU)

(73) Assignee: 8I RESEARCH DEVELOPMENT PTY LTD, Castlecrag (AU)

( * ) Notice: Subject to any disclaimer, the term of this patent is extended or adjusted under 35 U.S.C. 154(b) by 288 days.

(21) Appl. No.: 16/333,644

(22) PCT Filed: Sep. 19, 2017

(86) PCT No.: PCT/AU2017/000199
§ 371 (c)(1),
(2) Date: Mar. 15, 2019

(87) PCT Pub. No.: WO2018/049467
PCT Pub. Date: Mar. 22, 2018

(65) Prior Publication Data
US 2019/0255246 A1    Aug. 22, 2019

(30) Foreign Application Priority Data

Sep. 19, 2016 (AU) ................................ 2016903765
Apr. 24, 2017 (AU) ................................ 2017901496

(51) Int. Cl.
*A61M 5/168* (2006.01)
*A61M 3/02* (2006.01)
(Continued)

(52) U.S. Cl.
CPC ........ *A61M 3/0241* (2013.01); *A61M 3/0262* (2013.01); *A61M 5/1424* (2013.01);
(Continued)

(58) Field of Classification Search
CPC ........ A61M 2005/1403; A61M 3/0241; A61M 3/0262; A61M 5/1424; A61M 5/16809; A61M 5/16881; A61M 2005/1406
See application file for complete search history.

(56) References Cited

U.S. PATENT DOCUMENTS 3,398,743 A    8/1968    Shalit
5,505,707 A    4/1996    Manzie et al.

FOREIGN PATENT DOCUMENTS

WO    2013/102236 A1    7/2011

OTHER PUBLICATIONS

Extended European Search Report (EESR) on the corresponding European application 17849915.8 dated Mar. 20, 2020.

*Primary Examiner* — Deanna K Hall
(74) *Attorney, Agent, or Firm* — Browdy and Neimark, PLLC (57) ABSTRACT

The invention provides a fluid management system (1) for providing fluid from a fluid source (20) to the body of a patient. The fluid management system (1) includes a compressible chamber (10). A fluid conduit (30) is in fluid communication with the fluid source (20) and with an interior of the compressible chamber (10). A bypass conduit (40) has an inlet end (43) in fluid communication with the fluid source (20) and an outlet end (44) for providing fluid to a trocar (70). The bypass conduit 40 passes either through or around the compressible chamber (10). A first one way valve (80) can admit fluid from the fluid conduit (30) into the interior of the compressible chamber (10). A second one way valve (90) can admit fluid within the interior of the compressible chamber (10) into the bypass conduit (40). A portion (46) of the bypass conduit (40) upstream of the second one way valve (90) is collapsible under the force of selectively applied external pressure when the compressible chamber (10) is at least partially filled with fluid from the (Continued)

fluid source (20), so as to selectively close off the bypass conduit (40) upstream of the second one way valve (90).

18 Claims, 5 Drawing Sheets

(51) Int. Cl.
    *A61M 5/142*     (2006.01)
    *A61M 5/14*     (2006.01)
(52) U.S. Cl.
    CPC ..... *A61M 5/16809* (2013.01); *A61M 5/16881* (2013.01); *A61M 2005/1403* (2013.01)

FLUID MANAGEMENT SYSTEM

FIELD

The present invention relates to a fluid management system for providing fluid from a fluid source to the body of a patient and in particular for use in providing irrigation fluid to a surgical site in the body of a patient. The surgical site may be accessed through a relatively small incision in the body in conjunction with an arthroscope, laparoscope or similar device. The fluid management system can be used in many other medical fields and settings which require efficient and safe fluid delivery, including but not limited to orthopaedics, urology, emergency and trauma medicine, ICU, and on general medical wards.

BACKGROUND

Certain surgical procedures, such as knee arthroscopy or other arthroscopic procedures or urological procedures are performed inside the body through a very small incision on the body. When performing surgery of this type, the surgical site is inside the body of the patient, therefore the surgical area must be observed remotely, for example by means of an optical fibre scope connected to a video monitor. Fluid is used to distend the body cavity/joint and provide a media to visualise the tissue. A known difficulty with performing any surgical procedure is that blood or tissue may obstruct the surgical view. It is therefore routine to flush the surgical site with a bolus of fluid to clear the optical field so as to facilitate observation and to enable the surgeon to complete the operation. For a successful and safe knee arthroscopy, for example, several factors are important: a clear optical field, constant fluid pressure, adequate fluid flow rates, an open system which can safeguard against tissue baro-trauma and a flushing mechanism to clear debris. A common setup for providing irrigation fluid to surgical sites consists of a two litre saline bag hung between 20-100 cm above the surgical site with a connecting tube and clamps between the saline bag and arthroscopic trocar. The pressure for driving the fluid to the surgical site is provided by the difference in elevation between the surgical site and the saline bag. Another commonly used system uses two one-way valves and a squeezable chamber to pump fluid to the arthroscopic trocar and works as a "closed" system. A closed system has several disadvantages associated with it; these include reduced fluid flow rates through the strictures being the one way valves and accumulation of excessively high pressures through the one way design. This leads to poor flow, fluctuating pressures and a poor visual field for the surgeon. Pressures in excess of 200 mm Hg can easily be generated through this conventional system, potentially leading to tissue barotrauma, capsular rupture, extravasation and compartment syndrome. In maneuvers like high knee flexion and placing the leg in a 'figure of four', both of which raise intra-articular pressures, there is no safety mechanism in the system to release pressure build up. Published research shows pressures as low as 28 mm Hg are enough for good visualisation during knee arthroscopy. A mean pressure of 70 mm Hg provides consistent and sustained capsular distention while pressures over 150 mm Hg should be avoided while carrying out these procedures.

WO2013/102236 concerns a manually operated medical pump in which a bypass conduit providing a continuous fluid flow is provided inside a pumping chamber so that it is not compressed and disturbed during manual pumping of fluid through the pumping chamber. However, there is a need for a fluid management system having increased versatility of fluid flow rate and pressure.

It is an object of the present invention to provide a fluid management system which fulfils the above need at least to an extent or which provides an improved alternative.

SUMMARY OF INVENTION

Accordingly, the invention provides a fluid management system for providing fluid from a fluid source to the body of a patient, including:
- a compressible chamber having an inlet end and an outlet end;
- a fluid conduit in fluid communication with the fluid source and with an interior of the compressible chamber;
- a bypass conduit having an inlet end in fluid communication with the fluid source and an outlet end adapted for providing fluid to a trocar, the bypass conduit passing either through or around the compressible chamber from the inlet end to the outlet end thereof;
- a first one way valve adapted to admit fluid from the fluid conduit into the interior of the compressible chamber and a second one way valve adapted to admit fluid within the interior of the compressible chamber into the bypass conduit;
- wherein a portion of the bypass conduit upstream of the second one way valve is adapted to be collapsible under the force of selectively applied external pressure when the compressible chamber is at least partially filled with fluid from the fluid source, so as to selectively close off the bypass conduit upstream of the second one way valve.

In an embodiment, the fluid within the bypass conduit can flow, uninterrupted, from the fluid source to the trocar. If the bypass conduit has a relatively large diameter, the fluid flow therethrough can be laminar and uninterrupted, without a significant pressure drop (in accordance with the Hazen-Williams equation), meaning that a flow having a consistent speed and pressure is achievable at the trocar.

In an embodiment, the bypass conduit passes through the compressible chamber from the inlet end to the outlet end thereof and the external pressure is manual pressure applied to the compressible chamber.

In an embodiment, the inlet end of the compressible chamber has an inlet in fluid communication with the fluid conduit and the fluid conduit and the bypass conduit are arranged as separate conduits relative to the compressible chamber. This is to allow the fluid flow and pressure in the bypass conduit to be uninterrupted while the compressible chamber is refilled with fluid provided via the fluid conduit. The result is a more laminar flow with a more consistent flow rate and pressure from the fluid source to the trocar via the bypass conduit than in the known closed system.

In an alternative embodiment the fluid conduit is disposed coaxially inside of the bypass conduit and passes through a side wall of the bypass conduit such that an outlet of the fluid conduit is in fluid communication with the interior of the compressible chamber.

In another embodiment, the bypass conduit passes around the compressible chamber from the inlet end to the outlet end thereof. The external pressure is manual pressure applied directly to the bypass conduit to compress it against the compressible chamber.

In an embodiment, the inlet end of the compressible chamber has an inlet in fluid communication with an outlet end of the fluid conduit.

In an embodiment, the bypass conduit includes an on/off valve disposed between the inlet end thereof and the inlet end of the compressible chamber.

In an embodiment, the fluid management system further includes a fluid reservoir adapted for fluid communication with the fluid source and with the inlet end of the bypass conduit and the inlet end of the fluid conduit.

In an embodiment, the compressible chamber is made of PVC, silicone or similar material.

In an embodiment the bypass conduit has an inner diameter that is equal to or greater than an inner diameter of the fluid conduit and/or an inner diameter of the fluid source outlet.

In an embodiment, the fluid source is arranged at a vertical height above the compressible chamber during use.

In an embodiment, the fluid is saline fluid, sterile water, blood or other liquid used in a medical surgical procedure.

In an embodiment, at least a portion of bypass conduit extending through or around the compressible chamber is made of a compressible material.

In an embodiment, each of the first one way valve and the second one way valve is a membrane valve or a ball valve.

BRIEF DESCRIPTION OF DRAWINGS

Preferred embodiments of the present invention will now be described, by way of examples only, with reference to the accompanying drawings wherein.

DESCRIPTION OF EMBODIMENTS

Figure 1:
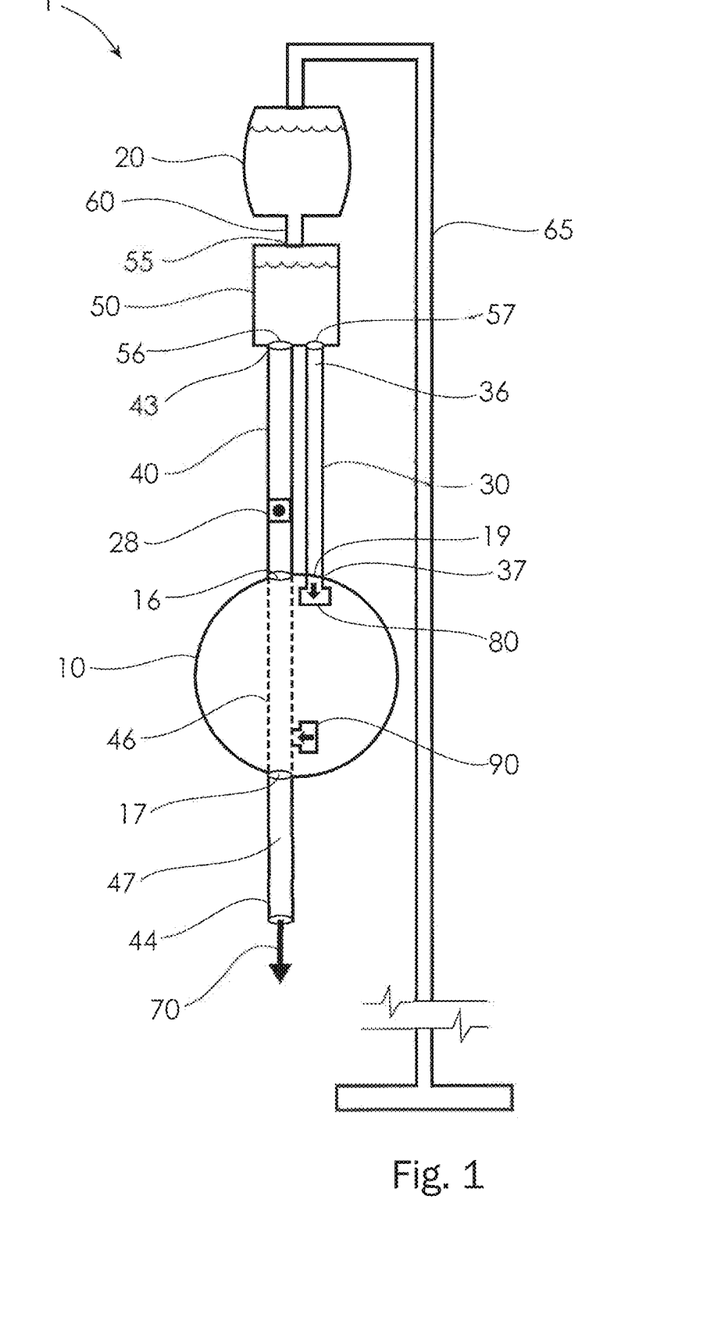
FIG. 1 shows a schematic front view of a first embodiment of a fluid management system.
Figure 2:
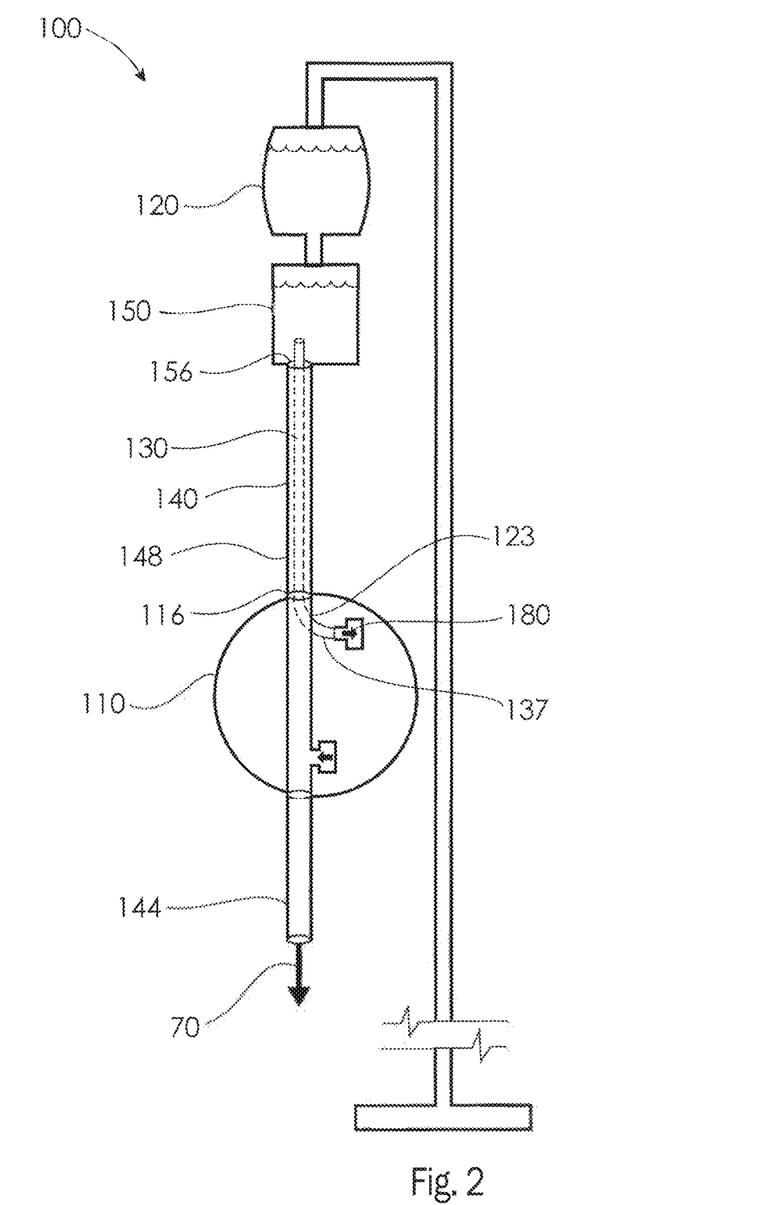
FIG. 2 shows a schematic front view of a second embodiment of a fluid management system.
Figure 3:
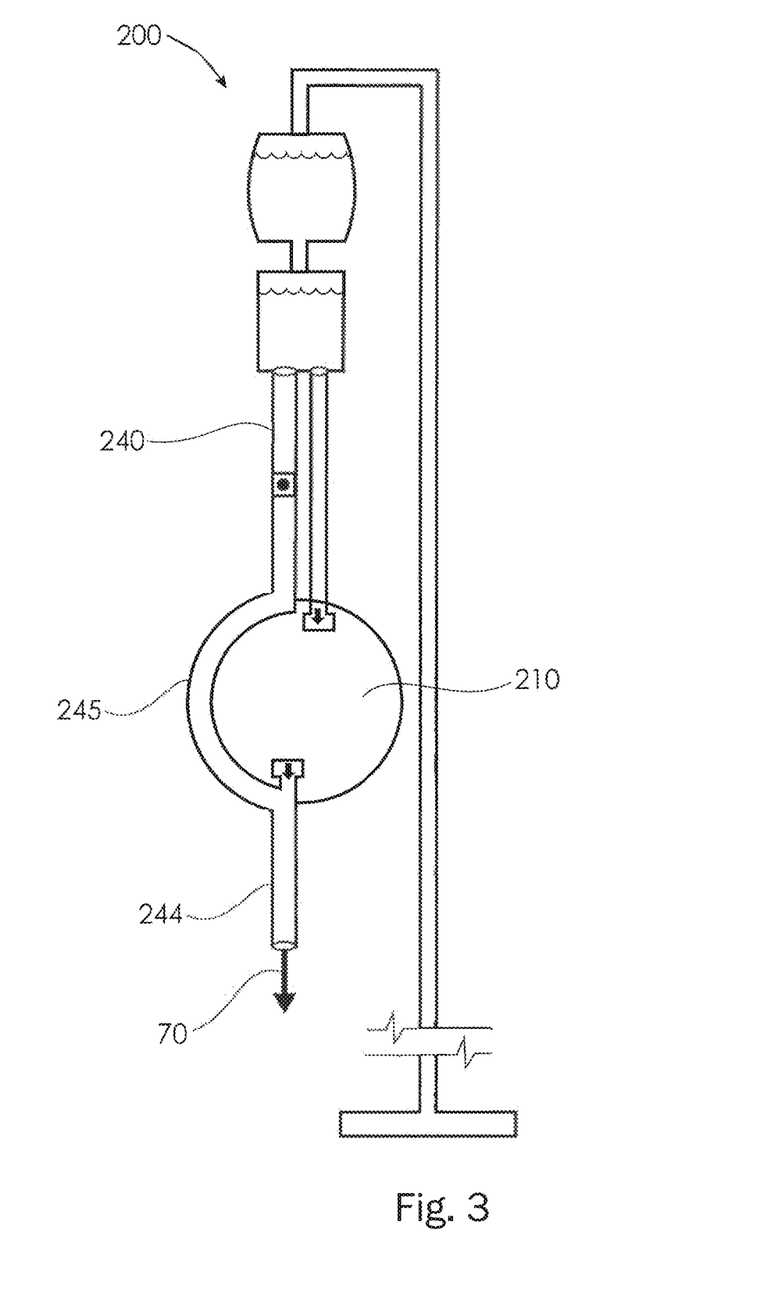
FIG. 3 shows a schematic front view of a third embodiment of a fluid management system.
Figure 4:
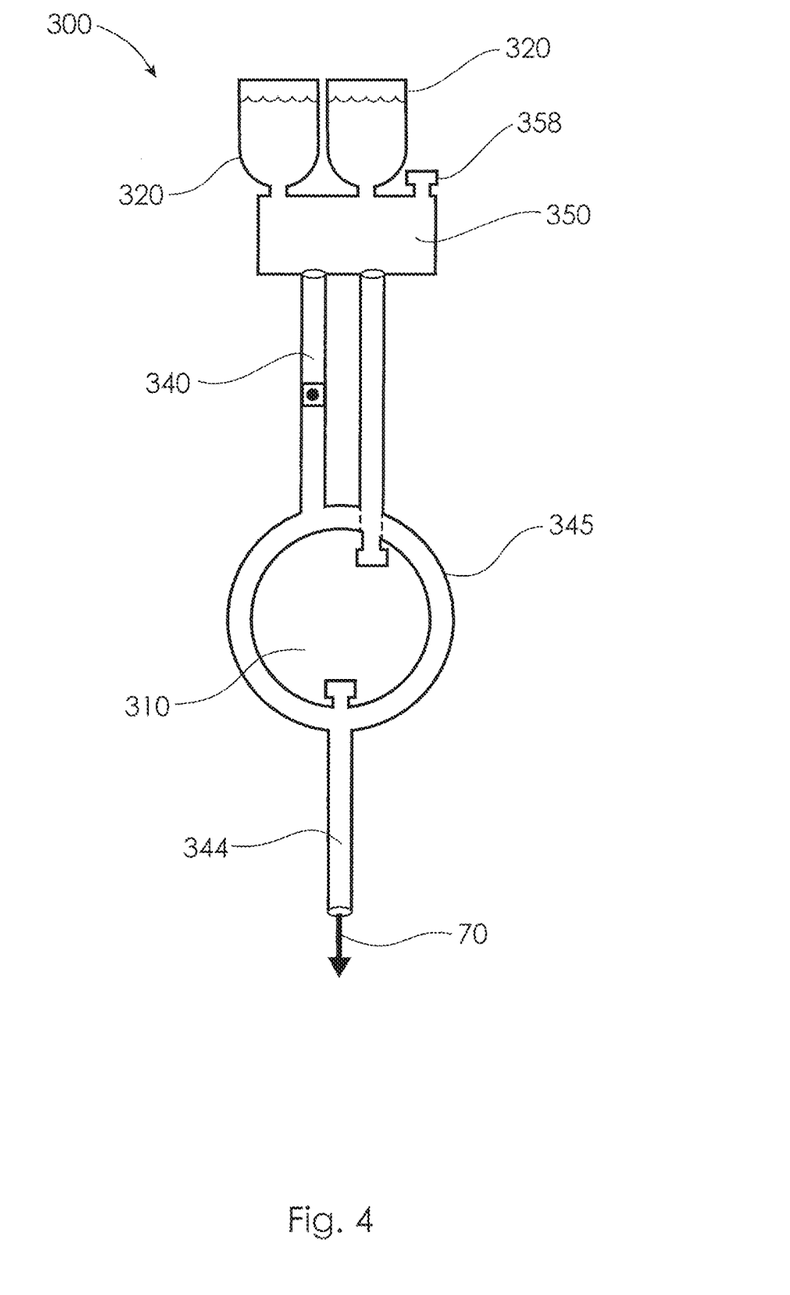
FIG. 4 shows a schematic front view of a fourth embodiment of a fluid management system.
Figure 5:
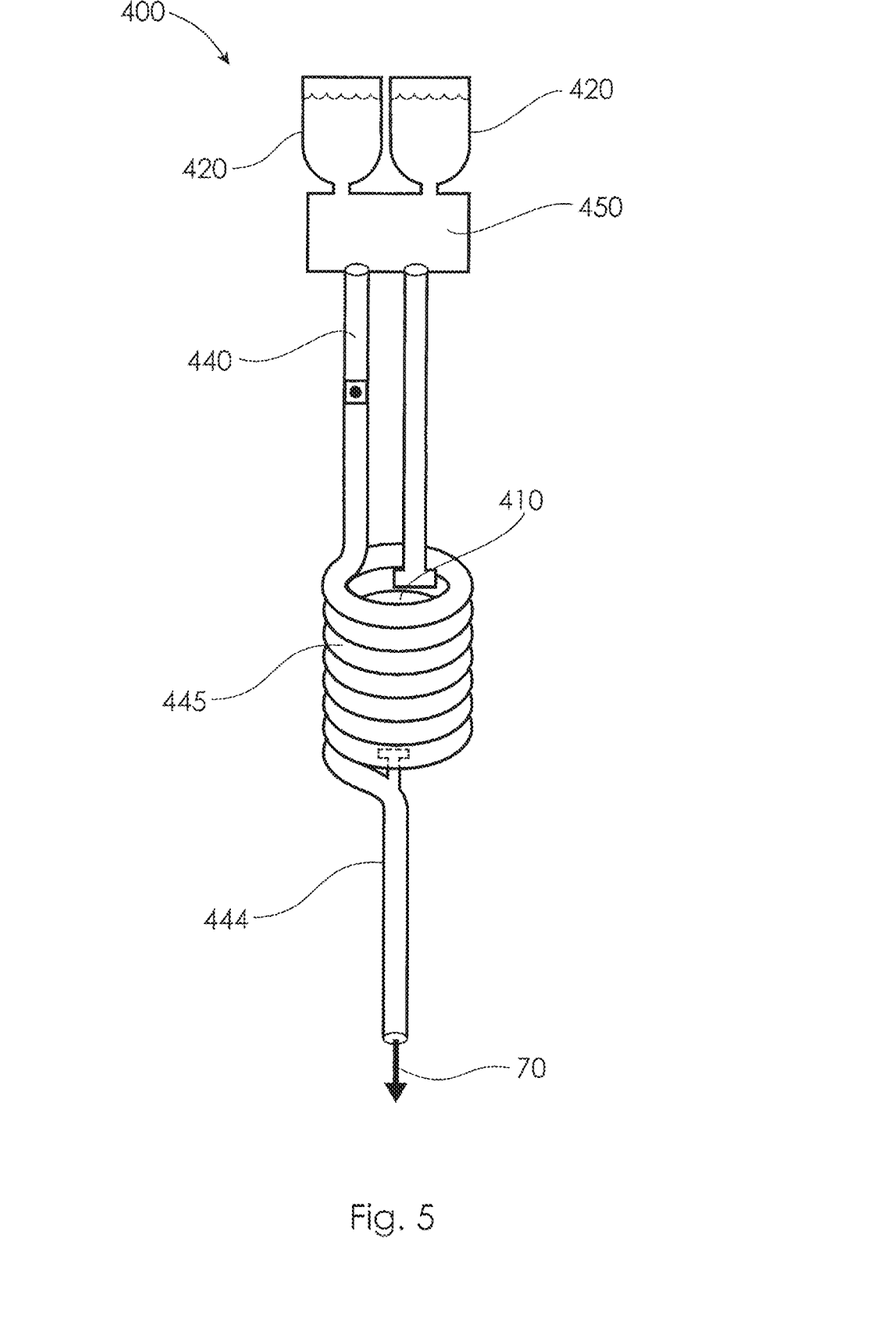
FIG. 5 shows a schematic front view of a fifth embodiment of a fluid management system.

It will be appreciated by a person skilled in the art that, although FIGS. 1 to 3 show a single fluid source, those embodiments can easily be used with plural fluid sources, as shown in FIGS. 4 and 5, for example.

FIG. 1 shows a first embodiment of a fluid management system 1 for use in providing irrigation fluid to a surgical site (not shown) on or in the body of a patient, during a surgical operation such as a knee arthroscopy.

The fluid management system 1 includes a compressible chamber 10, a fluid source 20, a fluid conduit 30, a bypass conduit 40 and a fluid reservoir 50.

The bypass conduit 40 and the fluid conduit 30 each consist of a length of PVC tubing. The bypass conduit 40 has an inlet end 43 and an outlet end 44, and the fluid conduit 30 has an inlet end 36 and an outlet end 37. The bypass conduit 40 has a relatively wide inner diameter of 8 mm whilst the fluid conduit 30 has an inner diameter of 6 mm. The fluid reservoir 50 is a container having an inlet 55 at its upper end and a first outlet 56 and a second outlet 57 at its lower end. The inlet 55 of the fluid reservoir 50 is attached via a standard length of PVC tubing 60 to a standard 2 litre bag 20 of irrigation fluid (the fluid source), which is, for example saline fluid for use in irrigating the surgical site within the patient's knee. In use, the bag 20 is held in a vertically elevated position, for example on an IV pole 65 relative to the surgical site so as to provide a pressure head to the fluid contained within the bag 20. The first outlet 56 of the fluid reservoir 50 is attached to the inlet end 43 of the bypass conduit 40, whilst the second outlet 57 of the fluid reservoir 50 is attached to the inlet end 36 of the fluid conduit 30 such that fluid contained within the fluid reservoir 50 can flow via the force of gravity into both the bypass conduit 40 and the fluid conduit 30. The fluid reservoir 50 hangs beneath the bag 20 with the bypass conduit 40 and the fluid conduit 30 hanging vertically beneath the fluid reservoir 50.

The compressible chamber 10 is generally spherical or cylindrical shaped and is made of PVC or silicon rubber or other suitable compressible material. The compressible chamber 10 has an upper end opening 16 and a lower end opening 17 through which the bypass conduit 40 passes such that a middle portion 46 of the bypass conduit 40 is located within the compressible chamber 10 and such that a lower end of the bypass conduit 40 that includes the outlet end 44 protrudes out of the lower end opening 17 for connection with an arthroscopic trocar 70, shown only schematically in FIGS. 1-5. The compressible chamber 10 also has an inlet 19 at an upper end thereof through which the outlet end 37 of the fluid conduit 30 is received. A first one-way valve 80 is affixed to the outlet end 37 within the interior of the compressible chamber 10 for admission of fluid from the fluid conduit 30 into the compressible chamber 10. As the valve 80 is directional, fluid in the compressible chamber 10 is not permitted to flow back out of the compressible chamber 10 into the fluid conduit 30. A second one-way valve 90 is affixed to a side wall of the bypass conduit 40 at a location of the side wall that is within the compressible chamber 10 and close to the lower opening 17. The second one-way valve 90 provides a controlled means of admitting fluid from inside the compressible chamber 10 into the bypass conduit 40 without admitting fluid flow from the bypass conduit 40 into the compressible chamber 10. Each of the first one-way valve 80 and the second one-way valve 90 is a membrane flap valve, ball valve or similar. The first one-way valve 80 will normally remain open to allow filling of the compressible chamber 10 and will be caused to close only when the pressure inside the chamber 10 rises when it is squeezed. The second one-way valve 90 will normally remain closed. However, if the chamber 10 is squeezed until a certain threshold pressure is reached, the valve 90 will open, allowing fluid to pass from the chamber 10 into the bypass conduit 40.

A middle portion 46 of the bypass conduit 40 that is inside the compressible chamber 10 and upstream of the second one-way valve 90 is made of a compressible material. To achieve this the silicone or PVC wall of the bypass conduit 40 is thinned or softened so that it becomes compressible at the middle portion 46. The system can be tailored to a particular specialty. For example, a less compressible middle portion 46 would result in lower pressure rises at trocar 70 when chamber 10 is compressed due to more backflow through middle portion 46 and be suited, for example, to routine knee arthroscopies. A more compressible middle portion 46 would result in high pressure rises at trocar 70 when chamber 10 is compressed due to less backflow through middle portion 46 and be suited for more difficult procedures, for example, shoulder or hip arthroscopies. The degree of thinning or softening of the middle portion 46 is chosen accordingly. The middle portion 46 is reinforced in the vicinity of the second one-way valve 90 and the outlet end 17 of the compressible chamber 10 such that it does not compress under pressure applied in these areas. The middle portion 46 of the bypass conduit 40 can be made to compress to varying degrees to suit particular applications. For example, the middle portion 46 can be made such that a gentle squeeze will cause it to compress, or it can be made such that only a very forceful squeeze will cause it to compress. The bypass conduit 40 is sealed to the inlet opening 16 and the outlet opening 17 of the compressible chamber 10 and to the one-way valve 90 using glue or other sealant. Similarly, the fluid conduit 30 is sealed to the inlet 19 of the compressible chamber 10 using glue or other sealant. Where feasible, a one piece mould can be used to manufacture the various connections of the compressible chamber 10.

A twist lock on/off valve 28 is installed in the bypass conduit 40 between the inlet end 43 and the inlet 16 of the compressible chamber 10. The lock on/off valve 28 is selectively used to close off the flow path through the bypass conduit 40 to the surgical site, leaving only the flow path through the compressible chamber 10 as will be described below. This allows the surgeon to switch to a fully closed system and generate higher pressures at the trocar 70.

Use of the fluid management system 1 is as follows. During normal usage in a surgical procedure, irrigation fluid in the bag 20 flows downwardly due to the force of gravity into the fluid reservoir 50, where it may collect for storage and later use. The fluid reservoir 50 may be omitted from the system, however it is useful as the fittings of the bag 20 and the diameter of the tubing 60 are of a standard size and cannot be changed. The inner diameter of the tubing 60 is narrow, effectively restricting the fluid flow rate out of the bag 20. The addition of the fluid reservoir 50 between the bag 20 and the fluid conduit 30 and bypass conduit 40 therefore allows fluid to be stored immediately upstream of the bypass conduit 40 and the fluid conduit 30 for use in the event that a greater fluid flow rate to the surgical site is required.

The lock on/off valve 28 is normally in an open position, permitting fluid to pass through the bypass conduit 40. The fluid within the bypass conduit 40 flows, uninterrupted, from the fluid reservoir 50 and into the arthroscopic trocar 70. The relatively large diameter of the bypass conduit 40 means that the fluid flow therethrough is laminar and uninterrupted, without a significant pressure drop (in accordance with the Hazen-Williams equation), meaning that a flow having a consistent speed and pressure is achievable at the arthroscopic trocar 70. This is particularly important in arthroscopic surgery. For the majority of a surgical procedure, fluid will be flowing from the higher pressure head of the fluid source 20 down to the trocar 70 and into the surgical site. However, there will be times when high pressures are generated at the surgical site and in the trocar 70, for example during high knee flexion, during which fluid can flow from the trocar 70 to the fluid source 20, thereby releasing the dangerous pressure and allowing it to equilibrate back to the pressure head of the fluid source 20.

A second flow path from the fluid reservoir 50 to the arthroscopic trocar 70 is via the fluid conduit 30. This flow path is akin to a conventional closed system, as it is automated by the one-way valves 80, 90. However, the presence of the compressible chamber 10 allows the fluid in this flow path to be pumped through to the trocar 70 at higher fluid pressure. The first one-way valve 80 at the inlet 19 normally remains open to allow fluid to fill the compressible chamber 10 unless a threshold pressure is generated by squeezing the compressible chamber 10, which pressure causes the valve to close and prevent backflow of fluid up the fluid conduit 30. Conversely, the second one-way valve 90 remains closed at all times unless a threshold pressure is generated by squeezing the compressible chamber 10, causing the valve 90 to open and allow fluid into the bypass conduit 40. The simultaneous compression of the compressible middle portion 46 of the bypass conduit 40 directs the fluid to the trocar 70 via the outlet 17 and the outlet 44 and not upstream to the fluid source 20. On releasing the pressure from the compressible chamber 10, the chamber 10 will rebound to its fully expanded shape. The negative pressure differential in the expanded compressible chamber 10 will cause the valve 90 to close and prevent fluid from being drawn into the compressible chamber 10 from the bypass conduit 40. This ensures that fluid flow and pressure from the bypass conduit is always uninterrupted. The negative pressure in the compressible chamber 10 and the pressure head in the fluid reservoir 50 will cause the one-way valve 80 to open and allow fluid to flow into compressible chamber 10 to refill.

At times during the surgical procedure, it is necessary to flush debris from the surgical site to maintain a clear optical field. At this time, a surgical assistant squeezes the compressible chamber 10. The compressible material of the chamber 10 means that manual pressure applied by the medical practitioner to the compressible chamber 10 is transferred to the fluid inside the compressible chamber 10. The fluid pressure in turn collapses the middle portion 46 of the bypass conduit 40 that is within the compressible chamber 10, closing off the back flow route up the bypass conduit 40 to the fluid reservoir 50. This has the effect of increasing the pressure differential at the one-way valves 80, 90, leading to an increased flow rate through the compressible chamber 10 and through a lower portion 47 and the outlet end 44 of the bypass conduit 40, thus a higher fluid pressure at the arthroscopic trocar 70. At this point in time the system behaves as a 'closed' system and then immediately reverts back to an 'open' system on releasing the manual pressure on the compressible chamber 10. The compressible chamber 10 restores its shape and immediately restores the bypass conduit 40/46 back to its normal open configuration, allowing fluid to pass freely between the fluid reservoir 50 and the trocar 70 to equilibrate to the pressure head of the fluid source 20. Manual pressure applied to the compressible chamber 10 therefore temporarily converts the open system to a closed system to instantaneously pump fluid through the chamber 10 at high pressure when it is required, however releasing the manual pressure on the chamber 10 instantly relieves the pressure, avoiding excessively high intra-articular pressures at the surgical site.

It will be appreciated that the collapsing of the middle portion 46 of the bypass conduit 40 temporarily creates a closed system within an increased fluid flow rate to flush debris and clear the optical field. The medical practitioner can release the pressure on the compressible chamber 10 at any time to safe guard against excessively high intra-articulate pressures. In this regard, the compressible chamber 10 can be made in varying sizes to deliver specific sized boluses to the arthroscopic trocar 70, for example boluses of 15 ml, 75 ml, 100 ml, 200 ml, etc. Accordingly, the system is able to provide a constant flow of fluids with boluses at any time necessary.

The twist lock on/off valve 28 is manually closed by the medical practitioner to further increase the fluid pressure of fluid passing through the compressible chamber 10 to the arthroscopic trocar 70, where deemed safe by the medical practitioner. In effect, closing the twist lock on/off valve 28 renders the bypass conduit 40 inactive, replicating the conventional one-way closed system to pump fluid at high pressures when required.

It will be appreciated that the wide diameter tubing utilized for the bypass conduit 40 creates adequate fluid flow rates following the Hazen-Williams equation governing the flow of water in a pipe and the pressure drop caused by friction. The wide diameter tubing allows for increased flow and more consistent pressures because it allows the system to quickly equilibrate to the pressure head of the fluid source 20. Markings on the tubing of the bypass conduit 40 can indicate safe pressures between, for example, 25 mm Hg and 100 mm Hg, that correlate to the height of the fluid source/bag 20 in accordance with the Hazen-Williams equation pertaining to head loss in water pipes.

FIG. 2 shows a second embodiment of the fluid management system 100 which has many features similar to that of the first embodiment 1. However, in the second embodiment of the fluid management system 100, the fluid conduit 130 is located coaxially within the bypass conduit 140 such that fluid exiting the fluid reservoir 150 at outlet 156 enters either one of the bypass conduit 140 and the fluid conduit 130. An outlet 156 enters either one or both of the bypass conduit 140 and the fluid conduit 130. An outlet end 137 of the fluid conduit 130 passes into the compressible chamber 110 and protrudes from a sealed orifice 123 in the side wall of the bypass conduit 140 close to the upper end opening 116 of the compressible chamber 110 such that the outlet end 137 of the fluid conduit 130 is in fluid communication with the interior of the compressible chamber 110. The outlet end 137 has a first one-way valve 180 associated therewith such that fluid within the fluid conduit 130 is permitted to enter the compressible chamber 110 via the one-way valve 180 as in the first embodiment 1. Fluid within the compressible chamber 110 is not permitted to flow back into the fluid conduit 130. Operation of the second embodiment 100 of the fluid management system is the same as that of the first embodiment 1, with the exception that there is no lock on/off valve in the upper portion 148 of the bypass conduit 140. The wide diameter of the bypass conduit 140 allows a constant flow rate of fluid through the upper portion 148 thereof that is uninterrupted by the presence of the fluid conduit 130 inside it, such that the same dual flow path is provided as with the first embodiment 1.

FIG. 3 shows a third embodiment of a fluid management system 200 which again has many features in common with the first embodiment 1 shown in FIG. 1. A fundamental difference between the third embodiment 200 and the first embodiment 1 is that the bypass conduit 240 no longer passes through the compressible chamber 210 but instead passes around it such that it is closely fitted over the compressible chamber 210. Accordingly, the bypass conduit 240 middle portion 245 follows the curvature of the compressible chamber 210. Operation of the third embodiment 200 of the fluid management system is the same as for the first embodiment 1. However, the collapsing of the middle portion 245 of the bypass conduit 240 occurs via manual pressure applied directly to it by the medical practitioner rather than via fluid pressure from within the compressible chamber 210. The fluid pressure within the compressible chamber 210 presses back on middle portion 245 of the bypass conduit 240 as manual pressure is applied to it, forcing the collapse.

FIG. 4 shows a fourth embodiment of a fluid management system 300 which is similar to the third embodiment shown in FIG. 3. A fundamental difference between the fourth embodiment 300 and the third embodiment 200 is that the middle portion 345 of the bypass conduit 340 completely encompasses all sides of the compressible chamber 310. Accordingly, the middle portion 345 follows the curvature of the compressible chamber 310.

Operation of the fourth embodiment 300 of the fluid management system is the same as for the third embodiment 200. The collapsing of the middle portion 345 of the bypass conduit 340 occurs via manual pressure applied directly to it by the operator. The fluid pressure within the compressible chamber 310 presses back on the bypass conduit 340 middle portion 345 as manual pressure is applied to it, forcing the collapse.

Fluid management system 300 includes two fluid sources 320, both feeding into fluid reservoir 350. A one way air valve 358 allows air in fluid reservoir 350 to be bled off.

FIG. 5 shows a fifth embodiment of a fluid management system 400 which again has many features in common with the first embodiment 1 shown in FIG. 1. A fundamental difference between the fifth embodiment 400 and the first embodiment 1 is that the bypass conduit 440 no longer passes through the compressible chamber 410 but instead passes around it such that it is closely fitted over the compressible chamber 410. In the fifth embodiment, the bypass conduit 440 middle portion 445 spirals around and follows the shape of the compressible chamber 410. The middle portion 445 is compressible and completely covers the compressible chamber 410. During manual compression of the compressible chamber 410, a part of the middle portion 445 is simultaneously compressed to varying degrees, depending on the force of the operator, which prevents backflow and increases pressure at trocar 70 to varying degrees.

As for FIG. 4, fluid management system 400 includes two fluid sources 420, both feeding into fluid reservoir 450.

In each of the embodiments 1, 100, 200, 300, 400, an optional secondary fluid bulb can be included closer to the arthroscopic trocar 70 and/or a pressure release valve can be included at the outlet end 44, 144, 244, 344, 444 of the bypass conduit 40, 140, 240, 340, 440 so that in the event of backflow from the knee or other surgical site into the trocar 70, debris will not block the compressible chamber 10, 110, 210, 310, 410.

INDUSTRIAL APPLICABILITY

Fluid management systems according to the above described embodiments exhibit improved and consistent fluid flow rates over the conventional closed irrigation systems, without the need for pumping. A clearer optical field can therefore be achieved, with more controlled and constant intra-articular pressure, thereby improving small vessel hemostasis. The open/automated closed system design prevents accumulation of dangerously high intra-articular pressures caused by an overzealous surgical assistant, however the facility to convert the open system to a temporarily closed system during manual pumping of the compressible chamber 10, 110, 210, 310, 410 also allows a means of pumping the fluid at suitably high pressures to instantly flush the surgical site with an equally instantaneous relief of the increased pressure flow upon manual release of the compressible chamber.

Although the invention has been described with reference to specific examples, it will be appreciated by those skilled in the art that the invention may be embodied in many other forms.

The invention claimed is:
1. A fluid management system for providing fluid from a fluid source to the body of a patient, including:

a compressible chamber having an inlet end and an outlet end;

a fluid conduit in fluid communication with the fluid source and with an interior of the compressible chamber;

a bypass conduit having an inlet end in fluid communication with the fluid source and an outlet end adapted for providing fluid to a trocar, the bypass conduit passing either through or around the compressible chamber from the inlet end to the outlet end thereof;

a first one way valve adapted to admit fluid from the fluid conduit into the interior of the compressible chamber and a second one way valve adapted to admit fluid within the interior of the compressible chamber into the bypass conduit;

wherein a portion of the bypass conduit upstream of the second one way valve is adapted to be collapsible under the force of selectively applied external pressure when the compressible chamber is at least partially filled with fluid from the fluid source, so as to selectively close off the bypass conduit upstream of the second one way valve.

2. A fluid management system as claimed in claim 1, wherein the bypass conduit is adapted to permit uninterrupted flow of fluid from the fluid source to the trocar.

3. A fluid management system as claimed in claim 1, wherein the bypass conduit passes through the compressible chamber from the inlet end to the outlet end thereof and the external pressure is manual pressure applied to the compressible chamber.

4. A fluid management system as claimed in claim 3, wherein the inlet end of the compressible chamber has an inlet in fluid communication with the fluid conduit, and wherein the fluid conduit and the bypass conduit are arranged as separate conduits relative to the compressible chamber.

5. A fluid management system as claimed in claim 3, wherein the fluid conduit is disposed coaxially inside of the bypass conduit and passes through a side wall of the bypass conduit such that an outlet of the fluid conduit is in fluid communication with the interior of the compressible chamber.

6. A fluid management system as claimed in claim 1, wherein the bypass conduit passes around the compressible chamber from the inlet end to the outlet end thereof and wherein the external pressure is manual pressure applied directly to the bypass conduit to compress it against the compressible chamber.

7. A fluid management system as claimed in claim 6, wherein the inlet end of the compressible chamber has an inlet in fluid communication with an outlet end of the fluid conduit.

8. A fluid management system as claimed in claim 1, wherein the bypass conduit includes an on/off valve disposed between the inlet end thereof and the inlet end of the compressible chamber.

9. A fluid management system as claimed in claim 1, further including a fluid reservoir with or without a one way air valve adapted for fluid communication with the fluid source and with the inlet end of the bypass conduit and the inlet end of the fluid conduit.

10. A fluid management system as claimed in claim 1, wherein the compressible chamber is made of PVC, silicone or a like material.

11. A fluid management system as claimed in claim 1, wherein the fluid source is arranged at a vertical height above the compressible chamber during use.

12. A fluid management system as claimed in claim 1, wherein there is a plurality of fluid sources.

13. A fluid management system as claimed in claim 1, wherein the fluid is irrigation fluid such as saline fluid, sterile water, blood or other liquid used in a medical surgical procedure.

14. A fluid management system as claimed in claim 1, wherein at least a portion of the bypass conduit extending through or around the compressible chamber is made of a compressible material of variable compressibility.

15. A fluid management system as claimed in claim 1, wherein each of the first one way valve and the second one way valve is a membrane valve or a ball valve.

16. A fluid management system as claimed in claim 1, wherein the bypass conduit has one or more markings to indicate safe pressure correlating to the height of the fluid source.

17. A fluid management system as claimed in claim 1, wherein the bypass conduit has an inner diameter that is equal to or larger than an inner diameter of the fluid conduit and/or an inner diameter of an outlet for the fluid source.

18. A fluid management system as claimed in claim 1, wherein arrangement of the fluid conduit and the bypass conduit as separate conduits relative to the compressible chamber is adapted to allow fluid flow and pressure in the bypass conduit to be uninterrupted while the compressible chamber is refilled with fluid provided via the fluid conduit.

* * * * *